United States Patent

Marrucchi

Patent Number: 5,117,875
Date of Patent: Jun. 2, 1992

[54] METHOD AND DEVICE FOR MANIPULATING AND TRANSFERRING PRODUCTS BETWEEN CONFINED VOLUMES

[76] Inventor: Piero Marrucchi, Piazza Pitti No. 17, Firenze, Italy

[21] Appl. No.: 357,326

[22] Filed: May 25, 1989

[30] Foreign Application Priority Data

Jun. 2, 1988 [IT] Italy .................. 12495 A/88
Apr. 10, 1989 [IT] Italy ................... 9696 A/89

[51] Int. Cl.$^5$ .................. A61M 5/00; A61M 3/00
[52] U.S. Cl. ............................ 141/1; 141/97; 141/329; 141/319; 141/363; 141/383; 604/405; 604/411; 604/415; 604/905; 206/219; 285/3; 215/DIG. 8
[58] Field of Search ............ 604/905, 86, 87, 88, 604/405, 408, 411, 412, 413, 414, 415, 416; 206/219, 222; 141/1, 329, 330, 319, 320, 321, 322, 363, 364, 365, 286, 290, 301, 307, 309, 97, 98, 383, 384, 386, 387; 285/3, 4; 215/DIG. 8

[56] References Cited

U.S. PATENT DOCUMENTS

| | | | |
|---|---|---|---|
| 2,849,156 | 8/1958 | Mansted ................ | 141/330 X |
| 3,872,867 | 3/1975 | Killinger ............... | 604/413 |
| 3,902,489 | 9/1975 | Carter .................. | 604/905 X |
| 3,986,508 | 10/1976 | Barrington ............ | 604/905 X |
| 4,019,512 | 4/1977 | Tenczak ................ | 604/905 X |
| 4,056,116 | 11/1977 | Carter et al. ......... | 604/905 X |
| 4,105,142 | 8/1978 | Morris, Jr. ............ | 141/319 X |
| 4,133,314 | 1/1979 | Bloom et al. ......... | 604/405 |
| 4,201,208 | 5/1980 | Cambio, Jr. ........... | 141/329 |
| 4,410,321 | 10/1983 | Pearson et al. ....... | 604/88 X |
| 4,411,662 | 10/1983 | Pearson ................ | 604/411 |
| 4,418,945 | 12/1983 | Kellogg ................. | 604/905 |
| 4,432,755 | 2/1984 | Pearson ................ | 604/905 X |
| 4,443,215 | 4/1984 | Smith ................... | 141/1 X |
| 4,457,749 | 7/1984 | Bellotti et al. ....... | 604/411 X |
| 4,458,733 | 7/1984 | Lyons ................... | 141/1 |
| 4,463,875 | 8/1984 | Tepic ................... | 206/219 X |
| 4,475,900 | 10/1984 | Popovich et al. ..... | 604/905 X |
| 4,589,879 | 5/1986 | Pearson ................ | 604/411 |
| 4,671,331 | 6/1987 | Pruden .................. | 141/98 |
| 4,798,605 | 1/1989 | Steiner et al. ........ | 604/411 |

FOREIGN PATENT DOCUMENTS

| | | | |
|---|---|---|---|
| 0256640 | 2/1988 | European Pat. Off. ..... | 604/905 |
| 2329704 | 6/1973 | Fed. Rep. of Germany . | |
| 2331687 | 6/1973 | Fed. Rep. of Germany . | |
| 3210964 | 3/1982 | Fed. Rep. of Germany . | |
| 906711 | 5/1945 | France ................. | 141/329 |
| 7122179 | 6/1971 | France . | |
| 2293916 | 8/1976 | France ................. | 206/222 |
| 0126642 | 5/1984 | Hungary . | |
| 8400075 | 3/1984 | Sweden . | |
| 0091310 | 4/1984 | United Kingdom . | |

Primary Examiner—Ernest G. Cusick
Attorney, Agent, or Firm—McGlew & Tuttle

[57] ABSTRACT

One of the two confined volumes, for example the "supplying" one (2), is provided with a tubular perforating element (3) confined within a space closed by a diaphragm or perforable wall (503); the second confined volume (1) also has a perforable diaphragm (301); the surfaces of the two diaphragms (503, 301) directed towards the external environment are permanently bonded together after which the perforator (3) is manipulated from the outside so as to perforate the two diaphragms, placing in communication, via the tubular duct of the perforator, the confined environment of the supplying volume with that of the second volume.

5 Claims, 6 Drawing Sheets

METHOD AND DEVICE FOR MANIPULATING AND TRANSFERRING PRODUCTS BETWEEN CONFINED VOLUMES

FIELD OF THE INVENTION

The present invention relates to so-called "confined volumes" or "controlled volumes" or containers such as bags made of impermeable plastic material or flasks or bottles made of glass, plastic material or the like. These are filled in a sterile environment or otherwise packaged, with suitable solid, gaseous or liquid products, and hermetically sealed so as to prevent any contamination of the products contained therein by the external environment, or any contamination of the external environment by the products contained inside. Frequently the need arises for the contents of two or more such confined volumes to be mixed together, and very frequently such mixing must take place shortly before the mixture is used, since the mixed product can often be preserved only for a limited period of time.

BACKGROUND OF THE INVENTION

Currently, in order to solve the problem of mixing two or more products, be they liquid, solid or gaseous, contained in confined volumes, use is made of a third confined "containment" volume with dimensions such that it contains the confined volumes to be mixed. The "containment" volume has means, such as half pressure chambers or sheaths, connected in a hermetically sealed manner and penetrating inside the confined containment volume, which allows the operator to intervene from the outside in order to manipulate, under absolutely sterile conditions, the confined volumes contained therein. After introducing the confined volumes to be manipulated inside the containment volume, and after the latter has been sealed or hermetically closed, it is necessary to perform sterilization or a particle check of the internal space of the containment volume and of the external walls of the confined volumes to be manipulated. This operation may take as long as a few hours, after which the operator can manipulate the confined volumes inside the containment space.

As can be seen, it is a complex, laborious, long and costly operation which requires special equipment.

SUMMARY AND OBJECTS OF THE INVENTION

The object of the present invention is to simplify the mixing operation, reducing considerably the time and cost thereof and eliminating the need to use special equipment such as the containment volumes with associated sterilization plants. At the same time ensuring, nevertheless, that the manipulating operation has taken place under absolutely safe conditions from the point of view of sterility or non-contaminating nature of the manipulated products and/or protection of the personnel employed to manipulate these products.

The present invention therefore relates mainly to a method for manipulating products confined within conditioned volumes ("confined volumes") comprising the stages of:

a) associating with one of the confined volumes a perforating or piercing element provided with a duct, confined in turn inside a conditioned environment closed by a diaphragm which can be perforated by the perforating element, one surface of this diaphragm being directed towards the external environment;

b) providing the second confined volume with a closing diaphragm which can be perforated by the perforating element, one surface of the diaphragm being directed towards the external environment;

c) intimately bonding together the surfaces of the diaphragms directed towards the external environment;

d) operating the perforating element from the outside so as to perforate the two diaphragms bonded together, thus placing in communication, via the duct of the perforating element, the contents of the two confined volumes;

e) transferring, through the duct of the perforating element, the contents of one confined volume into the second confined volume.

The present invention also relates to a perforating element for implementing the method according to the invention.

The present invention also relates to a system for intimately bonding the external walls of the said perforable diaphragms.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

In all the examples, corresponding parts may be indicated by the same reference numbers.

Figure 1:
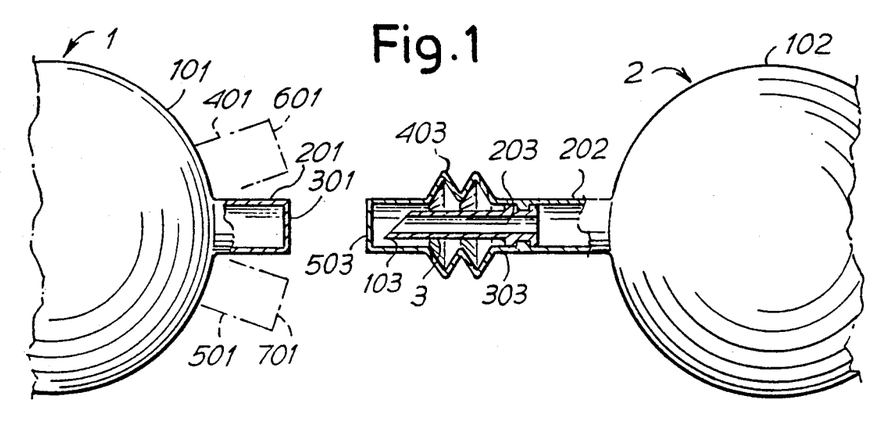
FIG. 1 is a diagrammatic view, with parts sectioned, of a system of two confined volumes according to the invention, illustrated during the stage preceding bonding of the external walls of their perforable diaphragms.

With reference to the drawings and with particular reference to FIG. 1 of the same, 1 denotes the first confined volume comprising a bag or bladder 101 made of impermeable elastic plastic material. The bladder 101 has a tubular attachment 201, integral therewith, communicating freely at one end with the internal space of the bladder 101 and closed at the other end by a diaphragm 301. Advantageously, both the bag 101 and the attachment 201 with the diaphragm 301 are made of polyvinyl chloride (PVC) or other suitable plastic material.

2 denotes the second confined volume. This second volume comprises, similar to the volume 1, a bladder 102 provided with a tubular attachment 202. Onto the free end of the attachment 202 there is fitted one end of a perforating or piercing element 3 terminating at its other end in a tip 103 shaped like a flute mouthpiece, or any other element designed to act as a perforating element. The tubular through-duct 203 of the perforating element 3 communicates freely with the internal space of the bladder 102.

The perforating element 3 is in turn accommodated with sufficient axial and radial movement within a tubular casing 303 made of elastic and flexible material, for example plastic, and provided, in its middle one, with a corrugated or bellows-type part 403. The tubular casing 303 is bonded at one end to the mouth of the attachment 202, while its other end is closed by a perforable diaphragm 503 entirely similar to the diaphragm 301 of the bladder 101 and made of the same material.

If it is assumed that it is required to transfer the contents of the bladder 102 (which will be referred to as the "supplying" bladder) into the bladder 101 ("receiving" bladder) in a completely aseptic manner, the procedure described below, with particular reference to FIGS. 2 and 3, will be adopted.

Prior to transferral, the diaphragms 301 and 503 must be intimately bonded together. For this purpose, it is possible to proceed in different ways which may depend, amongst other things, on the nature of the materials from which these diaphragms are made. One of the preferred materials for making these diaphragms is, as has been stated above, plastic material, for bonding of which a solvent thereof (such as cyclohexanone for example ) may be used. Therefore, the solvent is spread over the external surfaces of the diaphragms 301 and 503, after which these surfaces are made to adhere firmly together, as illustrated in FIG. 2. In order to obtain perfect adhesion over all the points of the surfaces of the two diaphragms making contact, it is possible to adopt certain measures, such as for example that consisting in making these surfaces slightly convex. In order to join them together, it is obviously possible to use a suitable support which holds them firmly together for the time necessary for bonding, or another system within the scope of any person skilled in the art.

Figure 3:
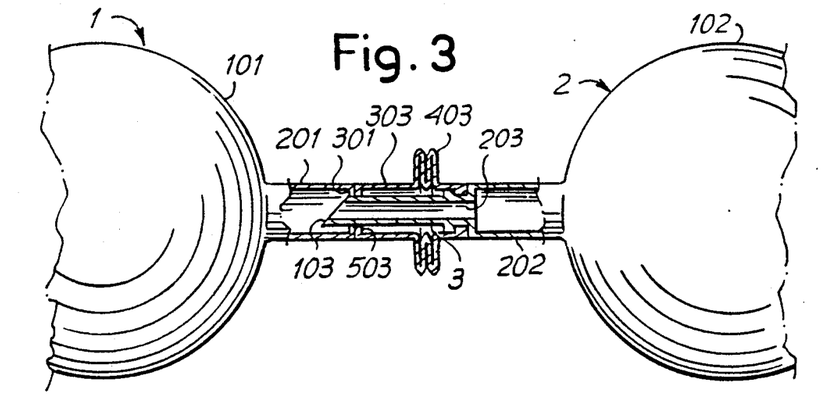
FIG. 3 is a view corresponding to those of FIGS. 1 and 2, illustrating the two confined volumes during the stage following operation of the tubular perforating element, or during the stage where communication is established between the two confined volumes.

After bonding the two external surfaces of the diaphragms 301 and 503, it is possible to establish the connection between the two confined volumes 1 and 2 by acting on the perforator 3 which is pushed against the diaphragms 301 and 503, taking advantage of the elastic characteristics of the tubular casing 303 and bellows 403, until the said diaphragms are completely perforated, as illustrated in FIG. 3. At this point, it is possible to cause the liquid to flow out from the supplying volume 2 into the receiving volume 3 in a completely conventional manner.

Once transferral has been completed, it is possible to seal, for example by means of a heat-bonding process, the attachment 201 upstream of the perforator 3 and then detach the confined volumes 1 and 2.

As illustrated in dot-dash lines in FIG. 1, branches 401, 501, provided at their ends with closing diaphragms 601, 701, may be connected to the attachment 201, said branches being used for connecting the confined volume 1 to other confined volumes similar to the volume 2, such that two or more different substances contained in the same number of confined volumes may be made to flow into this receiving volume.

Obviously, as regards the confined volumes 1 and 2, they have been shown and described as being provided with a single interconnection attachment (201, 202); it is obvious that they may be, and in general are, provided with a plurality of such attachments, both for the purpose of transferral and for the purpose of extraction for final use of the products confined therein.

Figure 2:
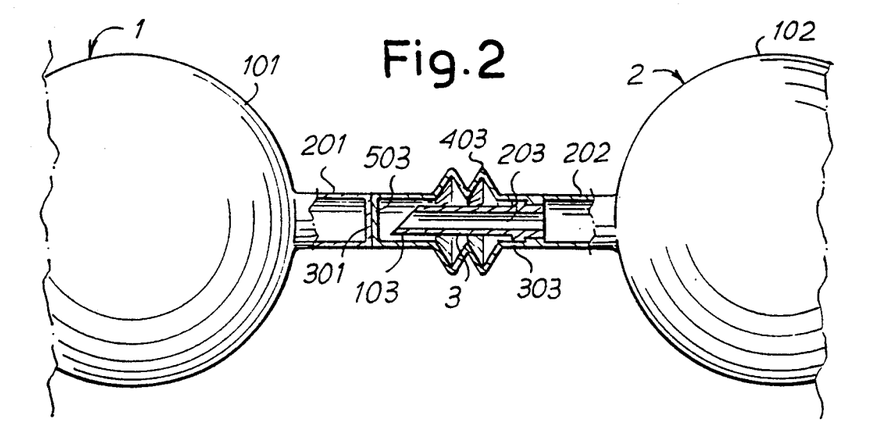
FIG. 2 is a view corresponding to that of FIG. 1, illustrating the two confined volumes during the stage where the external walls of their perforable diaphragms are bonded.
Figure 4:
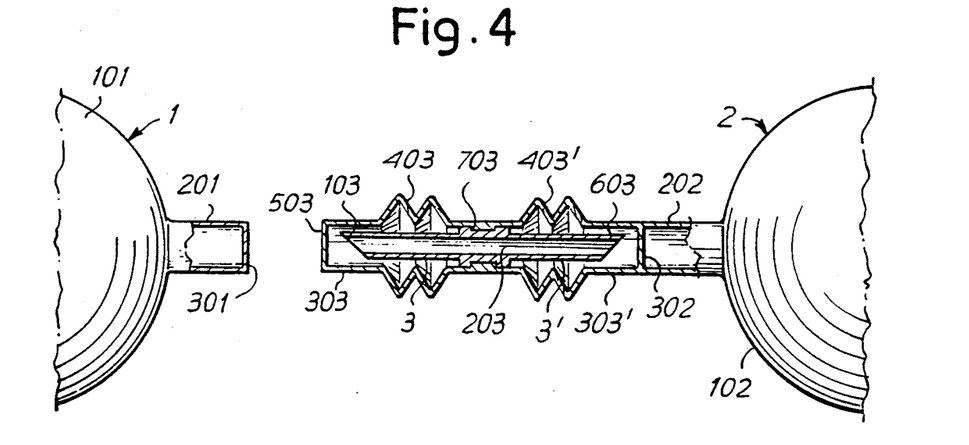
FIG. 4 is a view similar to that of FIG. 1, illustrating a modified embodiment of the perforating element.
Figure 6:
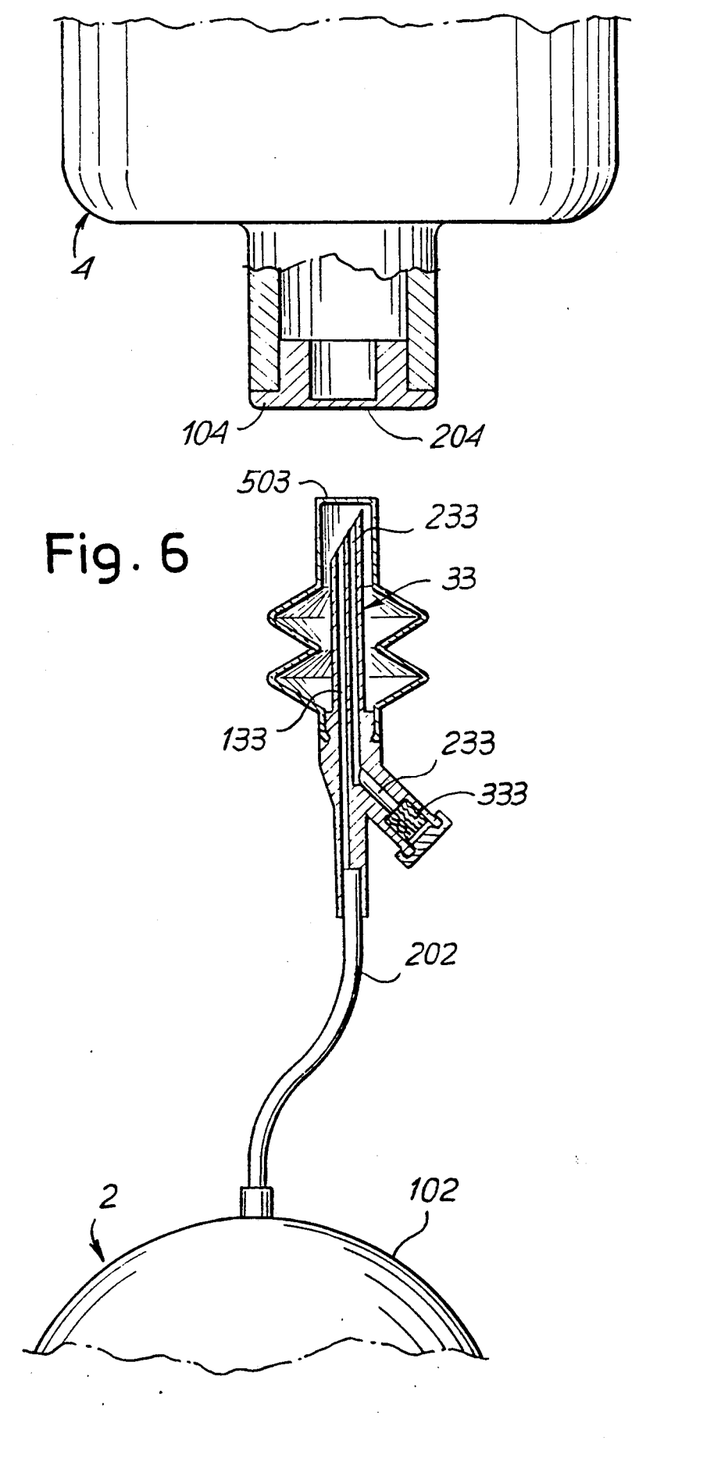
FIG. 6 is a view, similar to that of FIG. 1, of another variation of the invention.

FIGS. 4 and 6 show variations of the device of FIGS. 1 to 3. During the description of these variations, the same reference numbers will be used for parts which are the same as or correspond to those of the embodiment of FIGS. 1 to 3.

According to the embodiment of FIG. 4, the tubular attachment 202 of the confined volume 2 is closed by a diaphragm 302. A tubular casing 303, 303', provided with bellows-type parts 403, 403' and in turn closed at its end by the diaphragm 503, is connected to said tubular attachment 202. The tubular perforator 3, 3' is accommodated inside the tubular casing 303, 303' and bellows 403, 403'. This perforator 3, 3' is provided at both ends with pointed parts 103, 603 and is secured in the middle, by means of the element 703, to the tubular casing 303, 303'. The mode of operation of the device described will become apparent. Once the diaphragms 301 and 503 are bonded together, both the diaphragm 302 and the associated diaphragms 301, 503 are perforated, thus establishing communication between the two confined volumes 1 and 2, in a manner completely similar to that described with referred to the embodiment of FIGS. 1 to 3, acting on tubular casing 303,303'.

Figure 5:
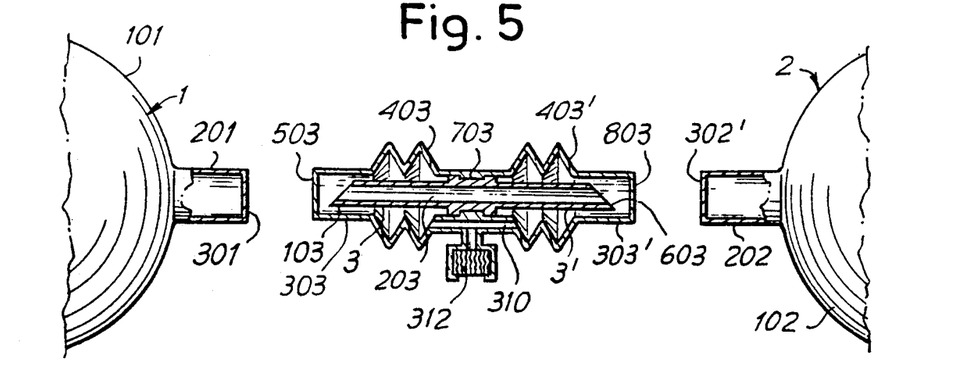
FIG. 5 is a view similar to that of FIG. 1, illustrating a further variation of the invention.

The embodiment shown in FIG. 5 is similar to that of FIG. 4, with the difference that the double perforator element 3, 3' is contained inside a confined volume separate from the volumes 1 and 2. For this purpose, the sleeve 303, 303' is closed at both ends by diaphragms 503, 803 and will have suitable inside conditions. In this case, in order for the confined volumes 1 and 2 to be operationally connected, the diaphragms 301 and 503, on the one hand, and 302' and 803, on the other hand, are bonded, thus effecting the connection between the confined volumes 1 and 2 in the manner described with reference to the embodiment of FIG. 4.

In order to simplify operation of the perforating element, the tubular casing 303, 303' may be provided with an air breather duct 310 connected to the external atmosphere via a suitable absolute filter 312.

In the examples of embodiment described above, the confinement elements have been illustrated and described as consisting of bags or bladders of soft plastic material which therefore allow transferral from one bladder to the other without problems.

FIG. 6 illustrates the case where at least one of the confinement elements or receptacles consists of a body with rigid undeformable walls and, for example, of a flask or bottle 4.

The bottle 4, which in the case illustrated consitutes the supplying confined volume, is closed by a stopper 104 provided centrally with a perforable diaphragm 204 which is suitably shaped and projecting. The received confined volume 2 is entirely similar to the volume 2 of FIG. 1, with the difference that the perforating element 33 has two channels passing inside it, namely a first channel 133 for transferral from the confined volume 4 to the volume 2, and a second channel 233 communicating with the external atmosphere via an absolute filter 333. The mode of operation of the device shown is moreover exactly the same as the mode of operation of the devices illustrated in the embodiments above, and provides an inlet for sterilized air (or any other suitable gas) in bottle 4.

The advantages of the method and the device described are obvious. They are, among others economic in nature, since the device according to the invention eliminates the need for using confined volumes within which the individual elements to undergo transferral must be introduced and manipulated, along with the associated sterilization equipment, etc., and considerable time losses.

However, they are also operational in nature, since they allow confined volumes to be manipulated in practically any environment and under any conditions, and with simple and fast operation.

In the above description, reference has been made to the bonding of diaphragms for the connection of the confined volumes by means of a product which is a solvent of the diaphragm itself. Obviously, this bonding may be performed in any manner suitable for the purpose, for example by means of heat-bonding or also using special glues which could even be of the self-adhesive type and could already be spread over the parts to be glued, protected by a suitable film which is removed at the time of use.

According to the illustrations of FIGS. 7 to 11, 1 and 2 denote the two confined volumes with tubular attachments 201 and 202; the attachment 202 forms a tubular casing 303 with a corrugated part so as to allow longitudinal deformations of the tubular casing 303 inside which the perforating element 903 extends. Said attachment 201 and said tubular with the attachment 202 form communication ducts with the two confined volumes 1 and 2. A membrane cap 1301, which forms the perforable diaphragm 301, is sealed on the end of the attachment 201. At its end, the casing 303 has, also formed as one piece, a similar membrane cap 1503, which forms the perforable diaphragm 503. The two diaphragms 301 and 503 must be coupled and bonded together.

Figure 7:
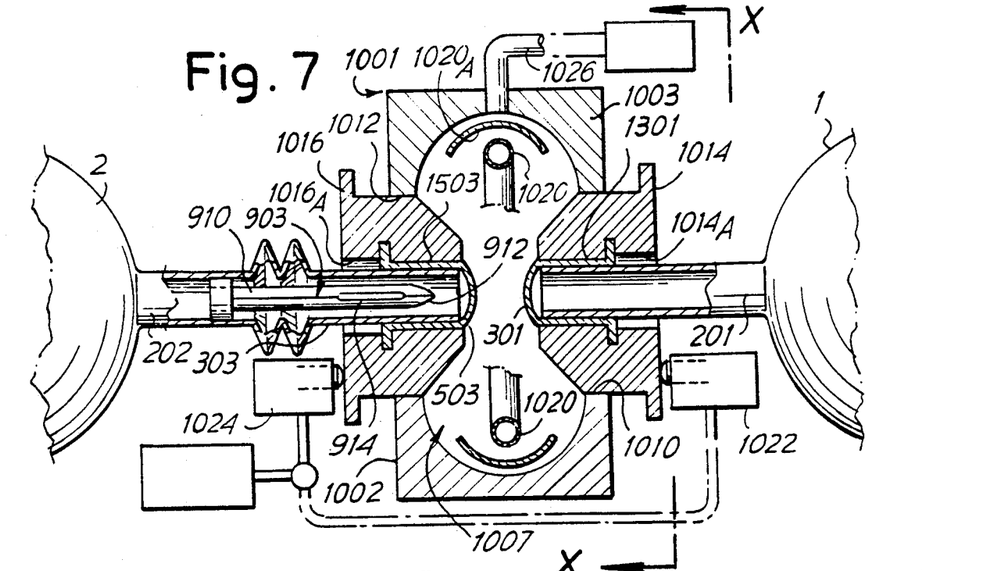
FIGS. 7, 8 and 9 show, in section, a device for effecting bonding in three successive operational stages.
Figures 8, 9:
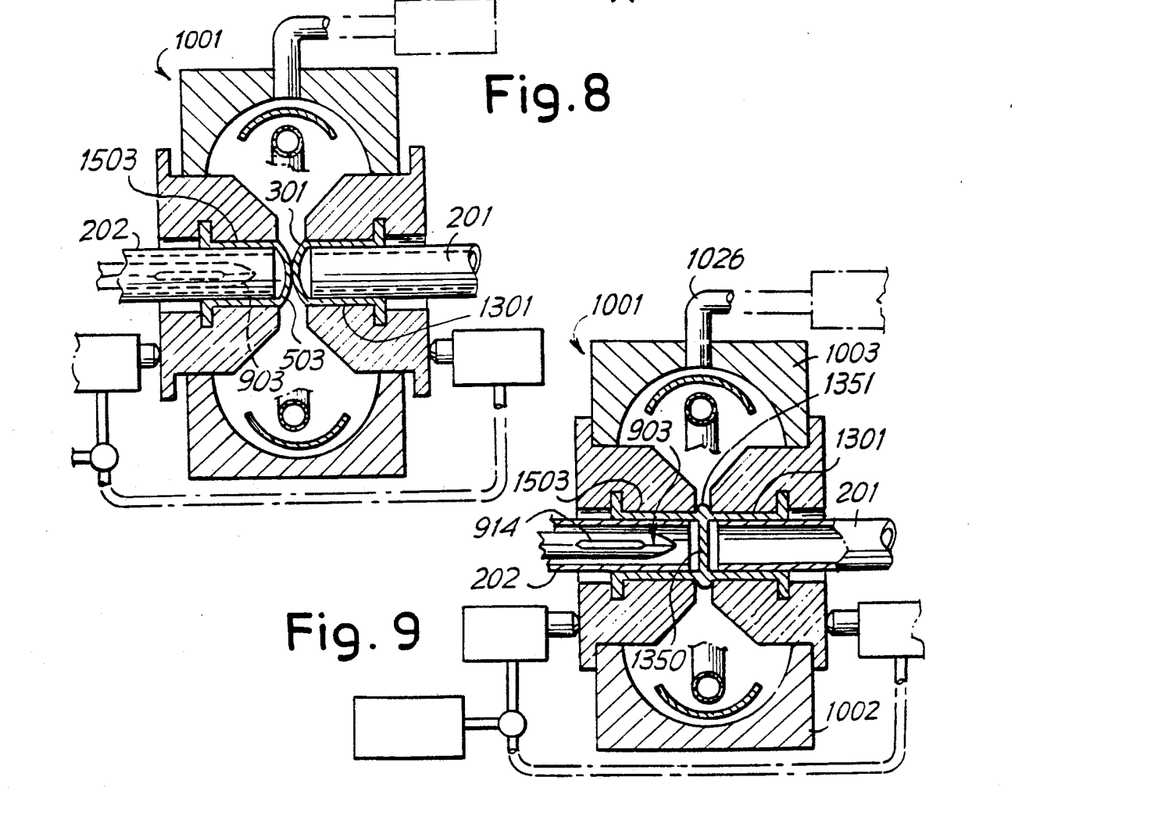

Said diaphragms are made of thermoplastic material and preferably are shaped with an outwards convexity with respect to the respective confined volumes; the caps 1301 and 1503 have collars projecting such that they are engaged by operating members described below.

The external surfaces of the two diaphragms 301 and 503 must be heated (FIG. 7) up to a level of plasticization sufficient to cause bonding between the two surfaces when brought into contact. The two heated surfaces are moved towards each other until initial localized contact is obtained (FIG. 8) in the center of the two diaphragms 301 and 503, this contact gradually increasing from the center towards the periphery until complete bonding occurs (FIG. 9). Compression which facilitates bonding of the two diaphragms is obtained by means of a pressure difference between the inside of the cavities formed by the attachment 201 and the casing 303, and the environment where the plasticized surfaces are located. Although it may be envisaged to create an excess pressure inside the cavities, preferably and advantageously it is envisaged to create a reduced pressure in said environment. This pressure difference is able to cause or ensure the convexity of the plasticized surfaces.

Bonding between the two diaphragms may be adjusted by modifying the heating temperature and/or the heating time and/or the mutual compression time and/or the pressure difference.

The two diaphragms coupled by means of bonding must be capable of being perforated by the perforator 903.

In order to achieve coupling by means of bonding, a device with a box 1001 consisting of two parts 1002 and 1003 which can be moved away and brought together and for example being articulated by a hinge 1005 may be provided; the box 1001 has a cavity 1007 having a symmetrical shape with respect to a geometrical axis of symmetry, which is horizontal in the drawing. The two parts 1002 and 1003 of the box 1001 in the closed condition define two opposite sliding seats 1010 and 1012 on the geometrical axis of symmetry, for slidably receiving two members 1014, 1016 with positioning seats 1014A and 1016A, respectively. Each of these members is divided into two halves and has a centrally through-recess which forms the seats 1014A and 1016A designed to engage with the corresponding membrane caps 1301 and 1503. The members 1014, 1016 position the diaphragms during the various stages of heating (FIG. 7), the bringing together and initial contact (FIG. 8) and the end position of bringing together and completing the bonding (FIG. 9), by means of the relative movement towards each other of the members 1014 and 1016 with positioning seats 1014A and 1016A.

For heating, an annular heating element 1020, in particular with an electrical resistance, is provided; it may consist of two halves carried by the two parts 1002 and 1003 of the box 1001 and may be associated with reflecting surfaces 1020A. Heating of the two surfaces of the diaphragms 301 and 503 occurs in a uniform manner, while the two diaphragms are kept separated (FIG. 1); suitable reflecting surfaces 1020A may be provided inside the cavity 1007 in order to irradiate the surfaces to be plasticized, for example formed by the walls of the cavity itself. After heating and superficial plasticization of the convex surfaces of the diaphragms 301 and 503, the latter are moved towards each other by moving their positioning members 1014 and 1016 closer together. This is advantageously obtained by creating a reduced pressure inside the cavity 1007, using vacuum means indicated by 1026; these means are able to cause a reduced pressure which is variable and in particular having increasing vacuum values. This reduced pressure acts on the members 1014 and 1016, so as to move them closer, if necessary against the action of counter springs and where appropriate with positive controlling movements over time via cam means or the like. The approach movement may also be obtained using positive means, such as those 1022, 1024, also providing a vacuum inside the cavity 1007. Alternatively, the approach movement may be obtained using mechanical or hydraulic means shown diagramatically in broken lines by 1022, 1024 and with counter springs, so as to achieve a positive operating action in accordance with a precise pattern of displacement. In each case, the reduced pressure inside the cavity 1007 facilitates the gradual bringing together, as described, of the two diaphragms 301 and 503—which have been superficially plasticized—starting from the point of initial contact visible in FIG. 8. The reduced pressure inside the chamber 1007 also tends to accentuate the convexity of the two diaphragms and cause compression of the two diaphragms.

At the end of the relative approach movement of the two members 1014 and 1016 within positioning seats 1014A and 1016A, complete fusion of the two diaphragms and hence formation of a single diaphragm 1350 is obtained (FIG. 9), without pockets or bubbles of air being trapped and with material, if necessary, being rejected, resulting in the formation of a perimetral swelling 1351, this being promoted by the reduced pressure The diaphragm 1350 is capable of being perforated by the perforator 903. Once the bonding operation has been complated, the two parts 1002 and 1003 of the box 1001 are moved away from each other and the positioning members are moved away, the members consisting of two parts for this purpose.

According to a possible variation of embodiment, only one of the two members 1014 and 1016 may be movable; the fixed seat for the non-displaceable cap may thus be formed directly by the two box parts 1002 and 1003.

FIGS. 7, 8, 9 and 11 show a perforator which has several ribs, for example three ribs 910, forming a tip with three cutting edges 912, which form an extension of the rounded edges of the three ribs 910. Longitudinal projections 914 extend between the ribs 910. The perforator 903 cuts the diaphragm with the three cutting edges 912; the opening is maintained by the three projections 914 in order to ensure transferral between the two confined volumes The coupling device, as described with reference to FIGS. 7 to 10, is simple and may be easily transported. This device is also suitable for the solutions of FIGS. 4, 5 and 6.

Figures 10, 11, 13:
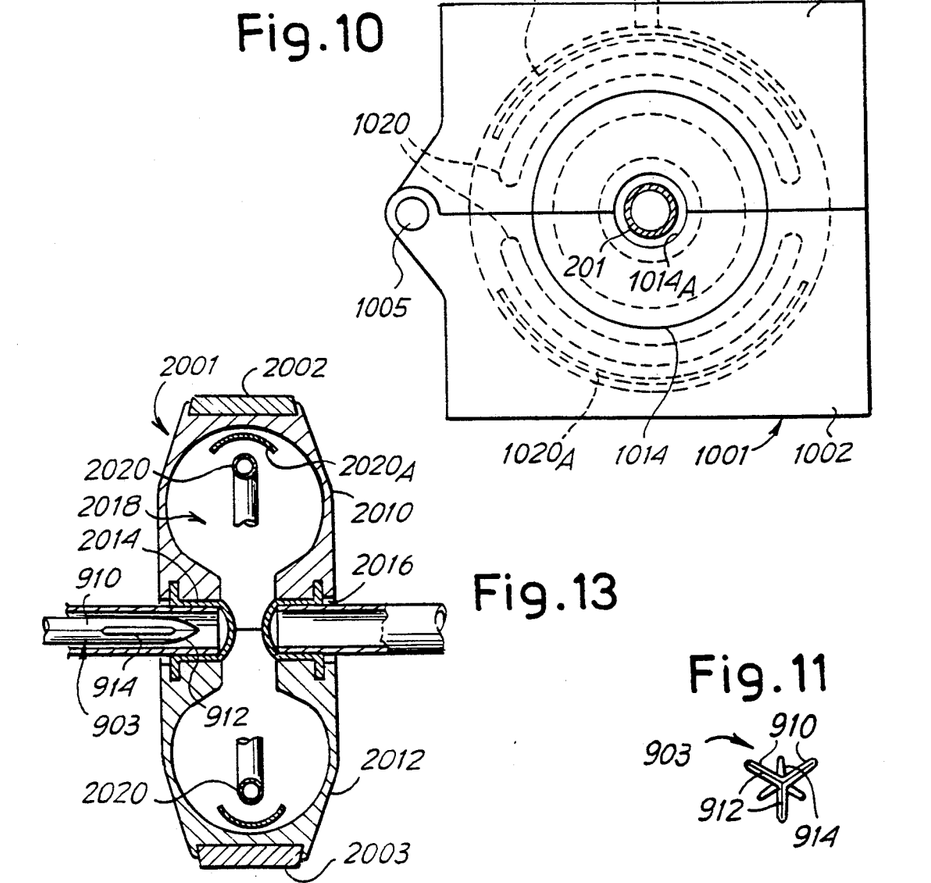
FIG. 10 is a view, in section, along X—X of FIG. 7.
FIG. 11 shows a detail of the perforator of FIGS. 7 to 10.
FIGS. 12 and 13 show a modified embodiment of the bonding device.
Figure 12:
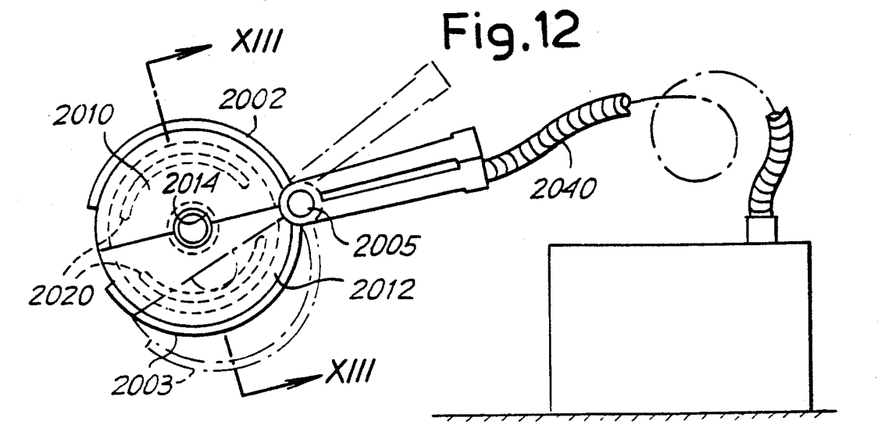

FIGS. 12 and 13 show a further embodiment of a bonding device, which may also be portable. On two arched supports 2002 and 2003, articulated at 2005 in the manner of pincers, there are engaged two half-shells 2010 and 2012 made of material which is at least partially flexible in the thinnest zones; the two half-shells 2010 and 2012 which form—when brought together—two coaxial and opposite positioning seats 2014 and 2016 designed to receive the components 303, 1503 and 201, 1301 (or the like). The two half-shells form a box 2001 and define, when brought together, an annular cavity 2018 where two heating elements 2020 are arranged, which complement each other annularly and which may be combined with reflecting surfaces 2020A. As a result of the flexibility of the half-shells 2010 and 2012, the two seats 2014 and 2016 may be axially moved towards and away from each other, owing to a reduced pressure created at the appropriate time inside the cavity 2018 and/or by means of an external operation, after heating and superficial plasticization of the opposing diaphragms 301 and 503 of the caps 1301 and 1503. The axial movements may be guided by the same shell formed by the half-shells 2010, 2012 or using sliding guiding means. The reverse of the approach movement may be obtained by the elastic return of the half-shells 2010 and 2012, or using a positive operating means not illustrated, or by means of an excess pressure inside the cavity 2018.

Inside the cavity 1007 or 2018 there may be introduced an atmosphere with special characteristics, for example a sterilizing atmosphere such as an oxidizing atmosphere, or an inert or vapor atmosphere, or an atmosphere of another type. This may be obtained using a flexible duct such as 1026 or 2040, by means of which it is possible to create the reduced pressure; separate ducts may also be envisaged.

The cavity 1007 or 2018 may also receive, if necessary, at least one source of corrective radiation, for example sterilizing the environment, so as to act on the surfaces of the diaphragms such as 301 and 503.

The term "manipulation" used in the description is intended to mean any operation performed on confined volumes and therefore also the transferral and/or emptying of the contents from one confined volume to the other.

The terms "sterile atmosphere" or "conditioned environment" or the like are intended to mean an environment free from pollution of any kind and, for example, also from particle contamination and/or contamination having particular environmental characteristics totally or partially incompatible with the external environment.

Insofar as the products contained in the confined volumes are mainly liquid, these volumes are also suitable for containing and manipulating solid or gaseous products, and the principles of the present invention apply equally well to these products.

The invention has been described mainly as being intended for the protection of the products contained in the confined environments from external influences. Obviously, it must also be understood that it is equally applicable for the protection and isolation of the external operators from the products contained in these environments.

When coupling is performed using adhesives, one of the confined volumes may be a living organism, the diaphragm of which is represented by the epidermis. One example is that shown in FIGS. 14 and 15.

Figures 14, 15:
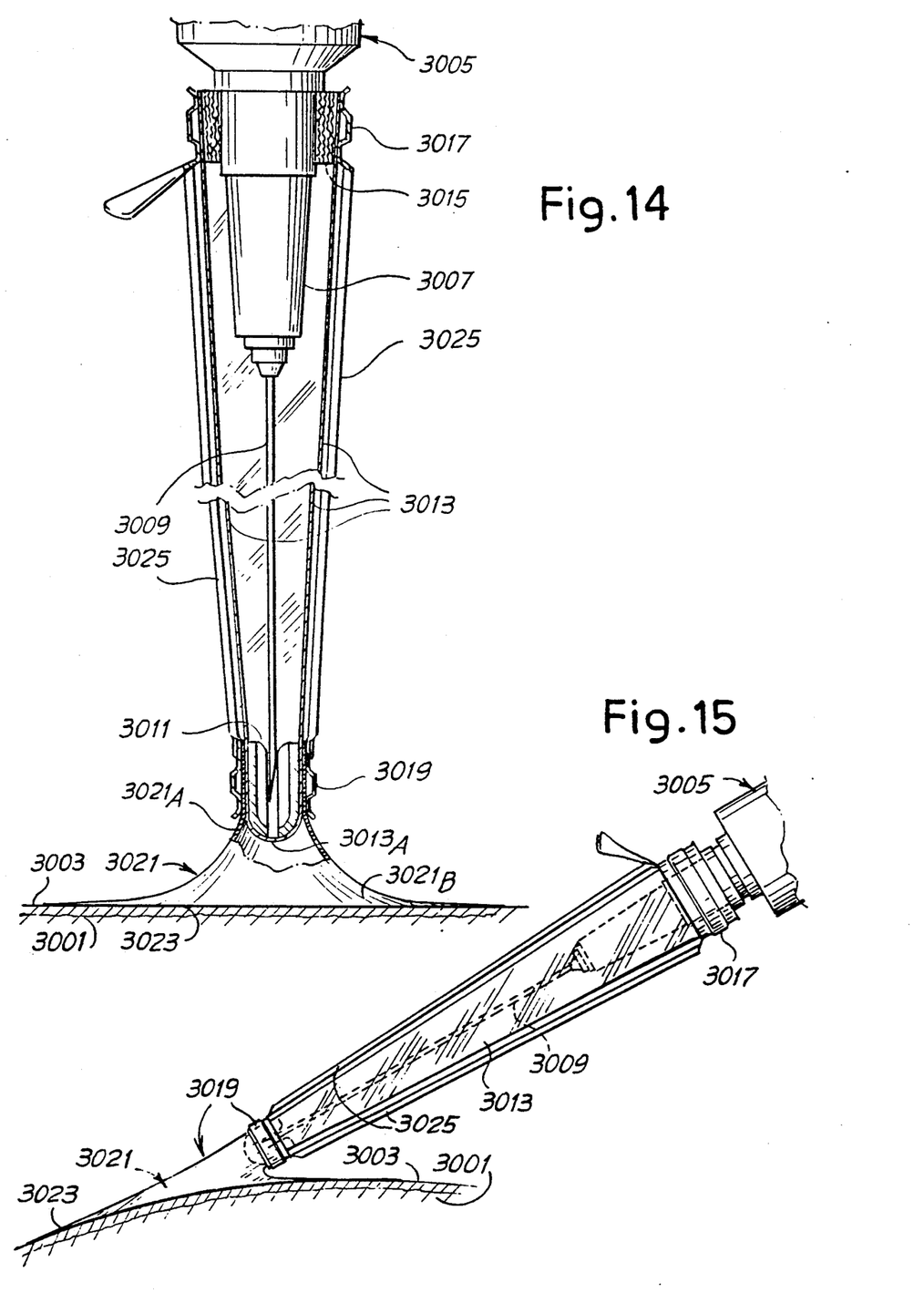
FIGS. 14 and 15 show another embodiment of the device.

FIGS. 14 and 15 show an embodiment in which one of the confined volumes is a living organism 3001, the epidermis of which, representing the diaphragm of this confined volume, is indicated by 3003. The device may be for example a syringe or bladder for introvenous injections, or an instrument for removing blood or other substance, which is indicated generally by 3005 and which forms one of the confined volumes. This device 3005 with an engaging body 3007 cooperates with a needle 3009. In the condition prior to use, the tip of the needle 3009 is surrounded by a protection ring 3011 provided with internal longitudinal ribs for effecting centering about the needle. A hood-type sheath 3013, which is elastic moreover (for example made of rubber latex) and semitransparent surrounds the needle 3009 and the protection ring 3011 and reaches the body 3007; the sheath 3013 surrounds a possible annular absolute filter 3015 surrounding the engaging body 3007; a clip 3017 clamps the sheath 3013 and the absolute filter 3015 on the body 3007. The absolute filter may also be made in another manner, or may be omitted. A further clip 3019 clamps, against the protection ring 3011, both the closed end of the hood-type sheath 3013 and the tubular central portion 8021A of a flexible and transparent film 3021, which gradually widens so as to form a flange 3021B with a flat edge; against this flange 3021B there is fixed a layer 3023 of transparent flexible material which acts as a diaphragm of the device 3005 and is designed to adhere to the epidermis and is, for example, self-adhesive. The closed end 3013A of the hood-type sheath 3013 and the adhesive layer 3023 may be perforated by the needle 3009. Between the two clips 3017 and 3019 there extend small rods 3025 or another rigid spacing element which serves to keep the clips separated until the moment of use.

When air must be discharged from the assembly 3007, 3005 through the needle 3009, the said air may be conveyed inside the hood-type sheath 3013 and from here discharged through the absolute filter 3015. Immediately after this first operation, where performed, the transparent layer 3023 is made to adhere to the adequately disinfected epidermis 3003 in the zone where the needle must be made to penetrate. The assembly may be inclined (FIG. 15), taking advantage of the possibilities offered by the film 3021, so as to cause penetration of the needle in the correct position, which can be controlled by means of the transparent layers 3021 and 3023. The needle 3009 is slid through the protection ring 3011 so as to perforate the bottom 3013A of the sheath 3013, the layer 3023 and the epidermis and so as to be inserted, where necessary, into the vein for the purposes of supply or removal. Once the operation has been completed, the needle is retracted until the tip of the ring 3011 is also withdrawn so as to locate a seat from where it is practically impossible for the tip to emerge again outside through the protection ring. The layer 3013A also tends to close again after extraction of the needle; the self-adhesive layer 3023, detached from the epidermis 3003 may be folded up and adhered to itself The external environment is thus protected.

An embodiment similar to that shown in FIGS. 14 and 15 may comprise a first cutting and/or perforating element for the diaphragms, which can be manipulated from the outside, and a further second element able to be inserted into the cut performed by the first element and to be maintained therein after withdrawal of the first element from the living organism. The second element ensures the communication with the confined volume 3005. The insertion of the second element may be performed simultaneously to the cutting or thereafter.

All those variations and modifications in design made to a device of the type described above and illustrated in the attached drawings are regarded as forming part of the present invention and as falling within the broadest scope of the inventive idea.

I claim:

1. A method of transferring products between two enclosed containers, the method comprising the steps of:
   enclosing a section of each of the containers by means of a pierceable thermoplastic diaphragm;
   providing the first container with a flexible section;
   positioning a piercing element having a through-duct inside the first container so that when said flexible section is compressed, said piercing element pierces said diaphragm of the first container;
   heating said diaphragms causing them to become adhesive;
   joining said heated adhesive diaphragms;
   cooling said joined diaphragms causing said cooled joined diaphragms to become firmly attached; and
   compressing said flexible section of the first container causing said piercing element to pierce said diaphragms, which have been joined, and causing products from one of the containers to transfer to the other container by means of said through-duct in said piercing element.

2. A method in accordance with claim 1, wherein:
   said diaphragms are convex-shaped when viewed from outside the containers.

3. A method in accordance with claim 1, further comprising:
   placing said diaphragms in an enclosed chamber prior to said step of said joining of said diaphragms; and
   reducing pressure inside said chamber, relative to the pressure inside the containers, causing said diaphragms to have a convex shape.

4. A method in accordance with claim 3, wherein:
   said reducing of pressure additionally causes said diaphragms to move toward each other and perform said joining step of said diaphragms.

5. A method in accordance with claim 1, further comprising:
   a plurality of pierceable thermoplastic diaphragms with a plurality of corresponding piercing elements and a plurality of corresponding flexible sections on a plurality of first containers;
   a plurality of the second type containers having a plurality of pierceable thermoplastic diaphragms; and
   heating, joining, piercing and transferring the products from a plurality of containers to another plurality of containers.

* * * * *